United States Patent
Kang et al.

(10) Patent No.: US 6,500,962 B1
(45) Date of Patent: Dec. 31, 2002

(54) PRODUCTION METHOD OF α-METHYLENE-γ-BUTYROLACTONES

(75) Inventors: Suk-Koo Kang, Gyeonggi-do (KR); Kwang-Jin Kim, Gyeonggi-do (KR)

(73) Assignee: Sungkyunkwan University (KR)

( * ) Notice: Subject to any disclaimer, the term of this patent is extended or adjusted under 35 U.S.C. 154(b) by 0 days.

(21) Appl. No.: 10/097,588

(22) Filed: Mar. 15, 2002

(30) Foreign Application Priority Data

Dec. 14, 2001 (KR) .............................................. 01-79423

(51) Int. Cl.⁷ ............................................. C07D 407/00
(52) U.S. Cl. ........................ 549/305; 549/306; 546/116; 548/453
(58) Field of Search ........................... 549/23, 50, 305, 549/306; 546/116; 548/453

(56) References Cited

PUBLICATIONS

Crowe, We et al, 'direct Synthesis of fused, bicyclic gamma–butyrolactones via tandem reductive cyclization—carbonylation of tethered enals and enones' J. Am. Chem. Soc. (1996), 118, 1557–58.*

* cited by examiner

*Primary Examiner*—Amelia Owens
(74) *Attorney, Agent, or Firm*—Burns, Doane, Swecker & Mathis, LLP

(57) ABSTRACT

The present invention relates to a method for producing an α-methylene-γ-butyrolactone which is one of basic structures often shown in drugs such as an anti-cancer agent by reacting an alene compound having an aldehyde or ketone group with carbon monoxide via cyclization in a single step in the presence of a catalyst containing ruthenium, thereby improving total yield of the entire reaction and achieving effects of cost reduction.

11 Claims, No Drawings

PRODUCTION METHOD OF α-METHYLENE-γ-BUTYROLACTONES

BACKGROUND OF THE INVENTION

1. Field of the Invention

The present invention relates to a novel method for synthesizing an α-methylene-γ-butyrolactone which is one of basic structures often shown in drugs such as an anticancer agent. More particularly, the present invention relates to a method for producing an α-methylene-γ-butyrolactone from an alene compound via cyclization in a single step using a catalyst containing ruthenium.

2. Description of the Related Art

The structure of an α-methylene-γ-butyrolactone can be found in many natural compounds having physiological activities. Particularly, sarkomycin, frullanolide and vernolepin of the following structures are representative substances having α-methylene-γ-butyrolactone structure and having excellent antibacterial and anticancer activities.

Further, it is known that physiologically active natural substances having the α-methylene-γ-butyrolactone structure constitute 10% of natural substances having anti-cancer activity (H. M. R. Hoffmann, et al., Angew. Chem. Int. Ed. Engl. 24(1985), 94–110).

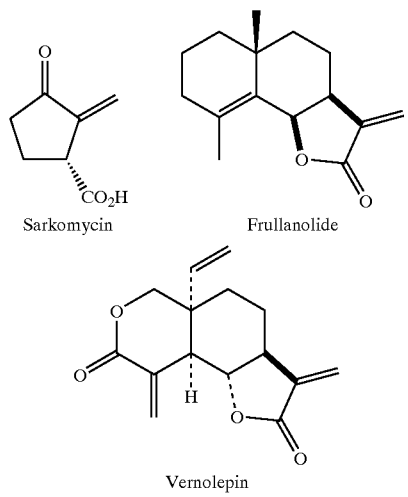

Sarkomycin    Frullanolide

Vernolepin

Thus, many methods for producing various α-methylene-γ-buytrolactones have been disclosed (see, for example, Crieco P., Synthesis 1975, 67–82). However, there has been disclosed no method using a catalyst such as ruthenium like in the present invention. In most of the known synthesis methods, products are obtained through many steps.

Now, synthesis methods largely involving two steps are known: a first step for forming bicyclic γ-lactone and a second step for introducing an α-methylene group. Among them, a representative method was reported by Buchwald and Crowe (J. Am. Chem. Soc. 1995, 117, 6785 and 1996, 118, 1557). According to them, the bicyclic γ-lactone is produced via a simultaneous [2+2+1] cyclization reaction by adding titanium in a stoichiometric equivalent to a ketone or aldehyde.

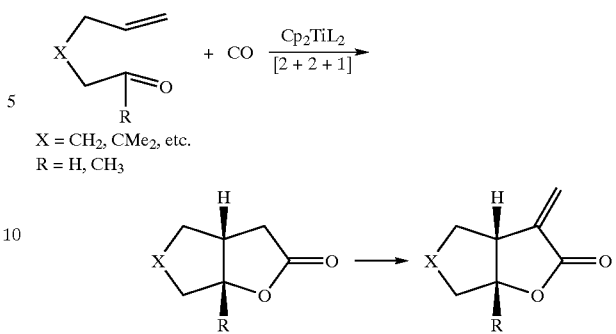

X = CH$_2$, CMe$_2$, etc.
R = H, CH$_3$

After formation of a γ-lactone ring using titanium in a stoichiometric equivalent, there is needed an additional step to introduce an α-methylene group in order to synthesize an α-methylene-γ-butyrolactone. This method has an advantage in that the synthesis methods in the prior art involving many steps are simplified to a two-step method comprising a first step to form a γ-lactone ring and a second step to introduce an α-methylene group. However, it has a disadvantage that the reaction using titanium is very unstable in the air and thus the reaction cannot be readily performed in the air. Further, although the methods are said to be roughly divided into two steps, in which a γ-lactone ring is firstly formed and an α-methylene group is introduced, in practice, at least two steps are needed to introduce the α-methylene group. Therefore, the reaction yeild is considerably reduced and expensive agents and much time are additionally used, thereby complicating the reaction and increasing production costs.

SUMMARY OF THE INVENTION

Therefore, an object of the invention is to provide a method for synthesizing an α-methylene-γ-butyrolactone by directly producing an α-methylene-γ-butyrolactone from an alene compound in a single step, thereby improving the entire reaction yield and reducing production costs.

In order to achieve the above object, there is provided a method for synthesizing an α-methylene-γ-butyrolactone by reacting an alene compound having the following formula (I) with carbon monoxide in the presence of a catalyst containing ruthenium:

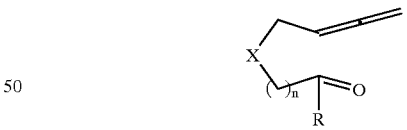

in which
R is hydrogen or C$_1$–C$_5$ low alkyl group;
X is selected from the group consisting of C, O, S and N, provided that when X is C, X is substituted with one selected from the group consisting of hydrogen, C$_1$–C$_5$ low alkyl and diethylester group, and when X is N, X is substituted with one selected from the group consisting of hydrogen, tosyl group, t-butyloxycarbonyl group and diethylester group; and n is 1 or 2.

DETAILED DESCRIPTION OF THE PREFERRED EMBODIMENT

Therefore, the present invention is directed to a method for synthesizing an α-methylene-γ-butyrolactone by reacting an alene compound having the following formula (I) with carbon monoxide in the presence of a catalyst containing ruthenium:

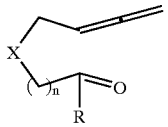

in which

R is hydrogen or $C_1$–$C_5$ low alkyl group;

X is selected from the group consisting of C, O, S and N, provided that when X is C, X is substituted with one selected from the group consisting of hydrogen, $C_1$–$C_5$ low alkyl and diethylester group, and when X is N, X is substituted with one selected from the group consisting of hydrogen, a tosyl group, t-butyloxycarbonyl group and diethylester group; and n is 1 or 2.

The α-methylene-γ-butyrolactone synthesized in a single step according to the present invention have the following formula (II):

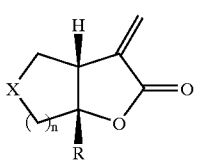

in which

R, X and n are the same as defined above.

R, X and n in the formula (I) and (II) according to the present invention are any of those known to be commonly used in α-methylene-γ-butyrolactones. In particular, a compound wherein X is N substituted with a tosyl group (Ts) or a t-butyloxycarbonyl group (t-BOC) or X is C substituted with a diethylester group (C(CO$_2$Et)$_2$).

The method according to the present invention is characterized by directly synthesizing an α-methylene-γ-butyrolactone via a [2+2+1] cyclization reaction in which an alene compound of the formula (I) is reacted with carbon monoxide in the presence of a catalyst containing ruthenium metal as shown in the following reaction scheme.

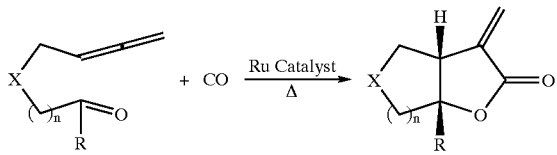

in which

R, X and n are the same as defined above.

The catalyst used in the method for producing an α-methylene-γ-butyrolactone according to the present invention is a catalyst containing ruthenium. It may be any of ruthenium-containing compounds known in the art. In particular, it may be preferably selected from the group consisting of Ru$_3$(CO)$_{12}$, [RuCl$_2$(CO$_3$)$_2$], RuCl$_2$(PPh$_3$)$_3$ and Cp$_2$Ru, most preferably Ru$_3$(CO)$_{12}$.

The used amount of ruthenium-containing catalyst may vary in a range of a commonly used catalytic amount and the specific amount depends on a type of the used ruthenium-containing catalyst. In general, it may be used preferably in about 0.1 to 10 mol % and particularly in about 1 to 3 mol %. The amount of the catalyst may be determined considering yield range and economic factors.

Carbon monoxide which is reacted with an alene compound of the formula (I) may be provided under conditions of high pressure. The specific pressure condition may be determined considering used reaction apparatus and equipments. In general, it may be preferably supplied at a pressure of about 10 to 30 atm.

The ruthenium catalytic reaction according to the present invention may be performed in the presence of an organic solvent. Any of organic solvents known to be usable in the production of α-methylene-γ-butyrolactone or in the ruthenium catalytic reaction can be used in the reaction in the present invention. Preferably, the solvent may be selected from the group consisting of dioxane, toluene and dimethyl formamide (DMF), particularly dioxane. Also, the ruthenium catalytic reaction according to the present invention may be performed at a temperature of about 100 to 150 for a suitable reaction time according to conditions of the used solvents, preferably for about 6 to 18 hours. The specific reaction time will be varied with amounts of the reacting compounds and other reaction conditions.

Now, the present invention will be described in detail using the following examples, which are provided only for illustration but not for limitation of the present invention thereto.

EXAMPLE 1

Synthesis of 3-methylene-5-(toluene-4-sulfonyl)-hexahydrofuro-(2,3-c)-pyrrole-2-one 0.80 g (3.0 mmol) of N-buta-2,3-dienyl-4-methyl-N-(2-oxo-ethyl)-benzene sulfoneamide [in the formula (I), n=1, R=H, X=NTs], 20 of dioxane and 20 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ethylacetate=1/1). Yield 0.66 g (75%).

Also, the target product was synthesized following the above procedure, except for using 20 of toluene as a solvent instead of dioxane. Yield 0.53 g (60%).

EXAMPLE 2

Synthesis of 3-methylene-2-oxo-hexahydrocyclopenta[b]furan-5,5'-dicarboxylic acid diethylester 0.80 g (3.15 mmol) of 2-buta-2,3-dienyl-2-(2-oxo-ethyl)-malonic acid diethylester [in the formula (I), n=1, R=H, X=C(CO$_2$Et)$_2$], 20 of dioxane and 20 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ethylacetate=1/1). Yield 0.53 g (60%).

EXAMPLE 3

Synthesis of 6a-methyl-3-methylene-5-(toluene-4-sulfonyl)-hexahydrofuro-(2,3-c)-pyrrole-2-one 0.80 g (2.86 mmol) of N-buta-2,3-dienyl-4-methyl-N-(2-oxo-propyl)-benzene sulfoneamide [in the formula (I), n=1, R=CH$_3$, X=NTs], 20 of dioxane and 18 (1 mol %) of Ru$_3$(CO)$_{12}$ were added to a stainless steel pressurizer and heated to a temperature of 120 at 20 atm of carbon monoxide for 17 hours. After completion of the reaction, solvent was removed under a reduced pressure and the product was purified by silica gel column chromatography (hexane/ ethylacetate=1/2). Yield 0.72 g (82%).

EXAMPLE 4

Synthesis of 6a-methyl-3-methylene-2-oxo-hexahydrocyclopenta[b]furan-5,5-dicarboxylic acid diethylester 0.80 g (3.0 mmol) of 2-buta-2,3-dienyl-2-(2-oxo-propyl)-malonic acid diethylester [in the formula (I), n=1, R=CH$_3$, X=C(CO$_2$Et)$_2$], 20 of dioxane and 19 (1 mol %) of Ru$_3$(CO)$_{12}$ were added to a stainless steel pressurizer and heated to a temperature of 120 at 20 atm of carbon monoxide for 17 hours. After completion of the reaction, solvent was removed under a reduced pressure and the product was purified by silica gel column chromatography (hexane/ ethylacetate=1/1). Yield 0.51 g (58%).

EXAMPLE 5

Synthesis of 3-methylene-5-(toluene-4-sulfonyl)-hexahydrofuro-(3,2-c)-pyridine-2-one 0.80 g (2.87 mmol) of N-buta-2,3-dienyl-4methyl-N-(2-oxo-propyl)-benzene sulfoneamide [in the formula (I), n=2, R=H, X=NTs], 20 of dioxane and 18 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ ethylacetate=1/1). Yield 0.53 g (60%).

EXAMPLE 6

Synthesis of 3-methylenetrihydrofuro-[3,2-c]pyran-2-one 0.80 g (3.0 mmol) of 3-buta-2,3-dienylpropyone aldehyde [in the formula (I), n=2, R=H, X=O], 20 of dioxane and 40 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ethylacetate=1/2). Yield 0.59 g (61%).

EXAMPLE 7

Synthesis of 3-methylene-2-oxo-hexahydrobenzofuran-5,5-dicarboxylic acid diethylester 0.80 g (3.0 mmol) of 2-buta-2,3-dienyl-2-(2-oxo-propyl)-malonic acid diethylester [in the formula (I), n=2, R=H, X=C(CO$_2$Et)$_2$], 20 of dioxane and 20 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ ethylacetate=1/2). Yield 0.49 g (55%).

EXAMPLE 8

Synthesis of 7a-methyl-3-methylene-2-oxo-hexahydrobenzofuran-5,5-dicarboxylic acid diethylester 0.80 g (2.83 mmol) of 2-buta-2,3-dienyl-2-(2-oxo-butyl)-malonic acid diethylester [in the formula (I), n=2, R=CH$_3$, X=C(CO$_2$Et)$_2$], 20 of dioxane and 18 (1 mol %) of Ru$_3$(CO)$_{12}$ were added to a stainless steel pressurizer and heated to a temperature of 120 at 20 atm of carbon monoxide for 17 hours. After completion of the reaction, solvent was removed under a reduced pressure and the product was purified by silica gel column chromatography (hexane/ ethylacetate=1/3). Yield 0.42 g (48%).

EXAMPLE 9

Synthesis of 3-methylene-2-oxo-hexahydrofuro-[2,3-c]-pyrrole-5-carboxylic acid t-butylester 0.80 g (3.79 mmol) of buta-2,3-dienyl-(2-oxo-ethyl)-carbamic acid t-butylester [in the formula (I), n=1, R=H, X=N(t-BOC)], 20 of dioxane and 24 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ ethylacetate=1/2). Yield 0.63 g (70%).

EXAMPLE 10

Synthesis of 3-methylene-2-oxo-hexahydrofuro-[3,2-c]-pyridine-5-carboxylic acid t-butylester 0.80 g (3.55 mmol) of buta-2,3-dienyl-2-(2-oxo-propyl)-carbamic acid t-butyl ester[in the formula (I), n=2, R=H, X=N(t-BOC)], 20 of dioxane and 23 (1 mol %) of Ru$_3$(CO)$_{12}$ were added to a stainless steel pressurizer and heated to a temperature of 120 at 20 atm of carbon monoxide for 12 hours. After completion of the reaction, solvent was removed under a reduced pressure and the product was purified by silica gel column chromatography (hexane/ ethylacetate=1/2). Yield 0.65 g (72%).

As described above, the single step synthesis method of an α-methylene-γ-butyrolactone using a ruthenium catalyst according to the present invention has not been known nor suggested in the prior art. By using the ruthenium catalyst according to the present invention, it is possible to produce an α-methylene-γ-butyrolactone from an alene compound having an aldehyde or ketone group via a cyclization reaction of a single step. Therefore, total yield of the entire reaction can be improved, thereby achieving effects of great cost reduction in the production process.

Also, since many anti-bacterial and anti-cancer active compounds having an α-methylene-γ-butyrolactone structure are known, the method according to the present invention may be applied to methods for producing such compounds. The present invention has a great utility in many industrial fields.

While the invention has been shown and described with reference to certain preferred embodiments thereof, it will be understood by those skilled in the art that various changes in form and details may be made therein without departing from the spirit and scope of the invention as defined by the appended claims.

What is claimed is:
1. A method for synthesizing an α-methylene-γ-butyrolactone by reacting an alene compound having the following formula (I) with carbon monoxide in the presence of a catalyst containing ruthenium:

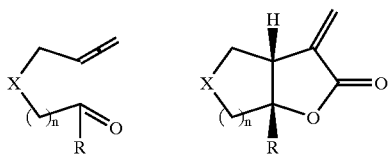

in which

R is hydrogen or $C_1$–$C_5$ low alkyl group;

X is selected from the group consisting of C, O, S and N, provided that when X is C, X is substituted with one selected from the group consisting of hydrogen, $C_1$–$C_5$ low alkyl and diethylester group, and when X is N, X is substituted with one selected from the group consisting of hydrogen, tosyl group, t-butyloxycarbonyl group and diethylester group; and n is 1 or 2.

2. The method as set forth in claim 1, wherein X is N substituted with any one selected from the group consisting of tosyl group and t-butyloxycarbonyl group.

3. The method as set forth in claim 1, wherein X is C substituted with diethylester group.

4. The method as set forth in claim 1, the catalyst containing ruthenium is any one selected from the group consisting of $Ru_3(CO)_{12}$, [$RuCl_2(CO_3)_2$], $RuCl_2(PPh_3)_3$ and $Cp_2Ru$.

5. The method as set forth in claim 3, wherein the catalyst containing ruthenium is $Ru_3(CO)_{12}$.

6. The method as set forth in claim 1, wherein the catalyst containing ruthenium is used in an amount of 0.1 to 10 mol %.

7. The method as set forth in claim 6, wherein the catalyst containing ruthenium is used in an amount of 1 to 3 mol %.

8. The method as set forth in claim 1, wherein the carbon monoxide is supplied at a pressure of 10 to 30 atm.

9. The method as set forth in claim 1, wherein the reaction is performed in the presence of a solvent selected from the group consisting of dioxane, toluene and dimethyl formamide.

10. The method as set forth in claim 9, wherein the solvent is dioxane.

11. The method as set forth in claim 1, wherein the reaction is performed at a temperature of 100 to 150.

* * * * *